United States Patent
Galloway et al.

[19]

[11] Patent Number: 5,831,143
[45] Date of Patent: Nov. 3, 1998

[54] METHOD FOR DETECTING HYDROGEN IN WASTE COMPOUNDS

[75] Inventors: Terry R. Galloway, Berkeley, Calif.; James R. Hensch, Richland, Wash.

[73] Assignee: The Scientific Ecology Group, Inc., Oak Ridge, Tenn.

[21] Appl. No.: 843,418

[22] Filed: Apr. 15, 1997

[51] Int. Cl.[6] ............................................. G01N 30/00
[52] U.S. Cl. .................. 73/19.01; 73/19.02; 73/23.41; 422/78; 422/80; 422/89; 436/144; 436/155; 436/161
[58] Field of Search ................ 73/19.01, 19.02, 73/23.41; 422/78, 80, 89; 436/144, 155, 157, 161

[56] References Cited

U.S. PATENT DOCUMENTS

| | | | |
|---|---|---|---|
| 3,173,762 | 3/1965 | Varadi et al. ....................... | 73/23.41 X |
| 3,177,700 | 4/1965 | Sier ....................................... | 73/19.01 |
| 4,244,917 | 1/1981 | Woods et al. ......................... | 422/89 X |
| 4,601,882 | 7/1986 | Benner ................................... | 422/80 |
| 4,654,171 | 3/1987 | Boncoeur et al. ................... | 436/57 X |
| 4,688,495 | 8/1987 | Galoway ............................... | 11/250 |
| 4,874,587 | 10/1989 | Galloway .............................. | 422/189 |
| 5,235,843 | 8/1993 | Langhorst ............................ | 73/19.1 X |
| 5,427,738 | 6/1995 | Galloway .............................. | 422/26 |
| 5,470,544 | 11/1995 | Galloway .............................. | 422/213 |

FOREIGN PATENT DOCUMENTS

| | | | |
|---|---|---|---|
| 58-113857 | 7/1983 | Japan ..................................... | 422/89 |

*Primary Examiner*—Daniel S. Larkin
*Attorney, Agent, or Firm*—John R. Lane, Esq.

[57] ABSTRACT

A method for determining hydrogen content in a compound is disclosed. This method generally comprises heating the sample to sufficient temperatures to effect pyrolytic conversion of any hydrogen containing compounds in the sample to hydrogen gas, and measuring the hydrogen content evolved by this conversion. In a preferred embodiment, this is carried out in a tube furnace inerted and purged with a noble gas. An apparatus for determining hydrogen content in a compound is also disclosed.

21 Claims, 5 Drawing Sheets

METHOD FOR DETECTING HYDROGEN IN WASTE COMPOUNDS

BACKGROUND OF THE INVENTION

1. Field of the Invention

The present invention generally relates to the field of treating and storing waste compounds including but not limited to medical, biohazardous, and nuclear waste. More specifically, the present invention is directed to the detection of hydrogen in these wastes, to ensure that these wastes are suitable for packaging, transport, and/or long-term storage.

2. Background Art

The storage of hazardous wastes such as certain organic compounds, chemical and biological warfare weapons, biomedical waste, and low and high level radioactive waste is an ongoing problem. The shipment of such waste to processing or disposal sites also creates a significant danger of environmental release in the event of an accident.

Present practices in the storage of spent solvents, activated carbon, heavy metals, radioactive, biomedical, and other hazardous waste, requiring pick-up and disposal through industrial waste haulers, has resulted in serious political and environmental problems for industries such as the chemical, nuclear, and electronic industries. Ground water contamination and occupational health problems have been steadily increasing. In addition, under the Federal Resource Conservation and Recovery Act (RCRA) there are long term legal risks to hazardous waste generators resulting from the ultimate fate of these materials, which is referred to as the "cradle-to-grave" responsibility of the generator. These problems are particularly prevalent in the nuclear industry. Long term-storage and decay of high level waste in repositories, as well as transportation in the U.S., requires under Nuclear Regulatory Commission (NRC) standards that less than 5%, or less than 0.593 gmoles, radiolytic hydrogen be generated by the waste as long as it is stored in a cask. In addition to being in violation of NRC regulations, failure to meet these hydrogen level requirements can result in unsafe transportation and storage conditions, possibly resulting in hydrogen overpressure and explosion of the storage casks. There are currently no accurate methods known for determining the amount of hydrogen that will be generated by waste during radiolytic decay. Because of the safety issues involved, there is a need, therefore, for a method to assay these wastes to determine if they are suitable for shipment and/or storage according to the NRC's strict regulations.

Numerous methods are aimed at the decomposition or other treatment of waste products for subsequent transport and/or storage. For example, U.S. Pat. No. 4,688,495 discloses a hazardous waste thermal decomposition reactor for treating solid, liquid, or gaseous waste products, converting said products to substances such as carbon dioxide, water and glassified non-leachable ash. U.S. Pat. No. 4,874,587 discloses a reactor system for decomposing organic compounds, and a method for using the same. U.S. Pat. No. 5,427,738 is generally directed to a system for detoxifying hazardous waste in which the waste is mechanically particularized to a predetermined particle size, and is then subjected to a gas flow having a temperature between about 250° C. and 750° C.; this results in gasification of a substantial portion of the solid waste. The remaining particularized waste residue is then collected for recycling or further disposal. U.S. Pat. No. 5,470,544 is directed to an apparatus for treating a liquid or slurry feed material. A bed of a plurality of independently movable surface-presenting bodies is moved through an exposure region, while circulating a gas stream through the bed from a gas input region to a gas output region in a direction substantially counter to the direction of the movement of the bed. The path is of a predetermined length selected to result in conversion of at least a portion of the feed material to an output product by reaction with the gas in the gas stream.

None of the above described methods or apparatus, however, include a method for determining the low level amount of hydrogen acceptable to the NRC that remains in the waste following treatment. Accordingly, there remains a need for such methods.

SUMMARY OF THE INVENTION

The present invention has met the above described need. The present invention relates to a method for determining the hydrogen content in a waste compound generally comprising the steps of inerting and purging a tube furnace with a noble gas, placing a sample of the waste compound to be tested in the furnace, heating the waste sample to a very high temperature in the presence of the noble gas to effect pyrolytic conversion of any hydrogen containing compounds in the waste sample to hydrogen gas, and determining the hydrogen content of the waste sample using gas chromatography, with the noble gas serving as the carrier. The novel analytical method described herein allows a treated waste product to be assayed in the field with both rapidity and high sensitivity. This allows the user to ensure that the strict NRC regulations concerning hydrogen content in waste are being met before the waste is placed and sealed in an inerted and slightly pressurized long-term storage cask. An apparatus for making this hydrogen determination is also disclosed.

It is therefore an object of the present invention to provide a method for determining the level of hydrogen in a compound.

A further object of the invention is to provide such a method for determining the level of hydrogen in waste compounds.

Another object of the present invention is to provide a method for detecting waste compounds that would form radiolytic hydrogen in unsafe amounts.

Another object of the present invention is to provide a highly sensitive method for determining the hydrogen content in waste compounds to ensure that less than 5% hydrogen is present in these wastes.

It is another object of the present invention to provide a method for determining hydrogen content in waste products suitable for use in the field.

It is a further object of the present invention to provide a method for determining the hydrogen content in steam-reformed nuclear residue products.

These and other objects of the invention will be apparent to those skilled in the art from the following description and claims.

DETAILED DESCRIPTION OF THE PRESENT INVENTION

Figure 1:
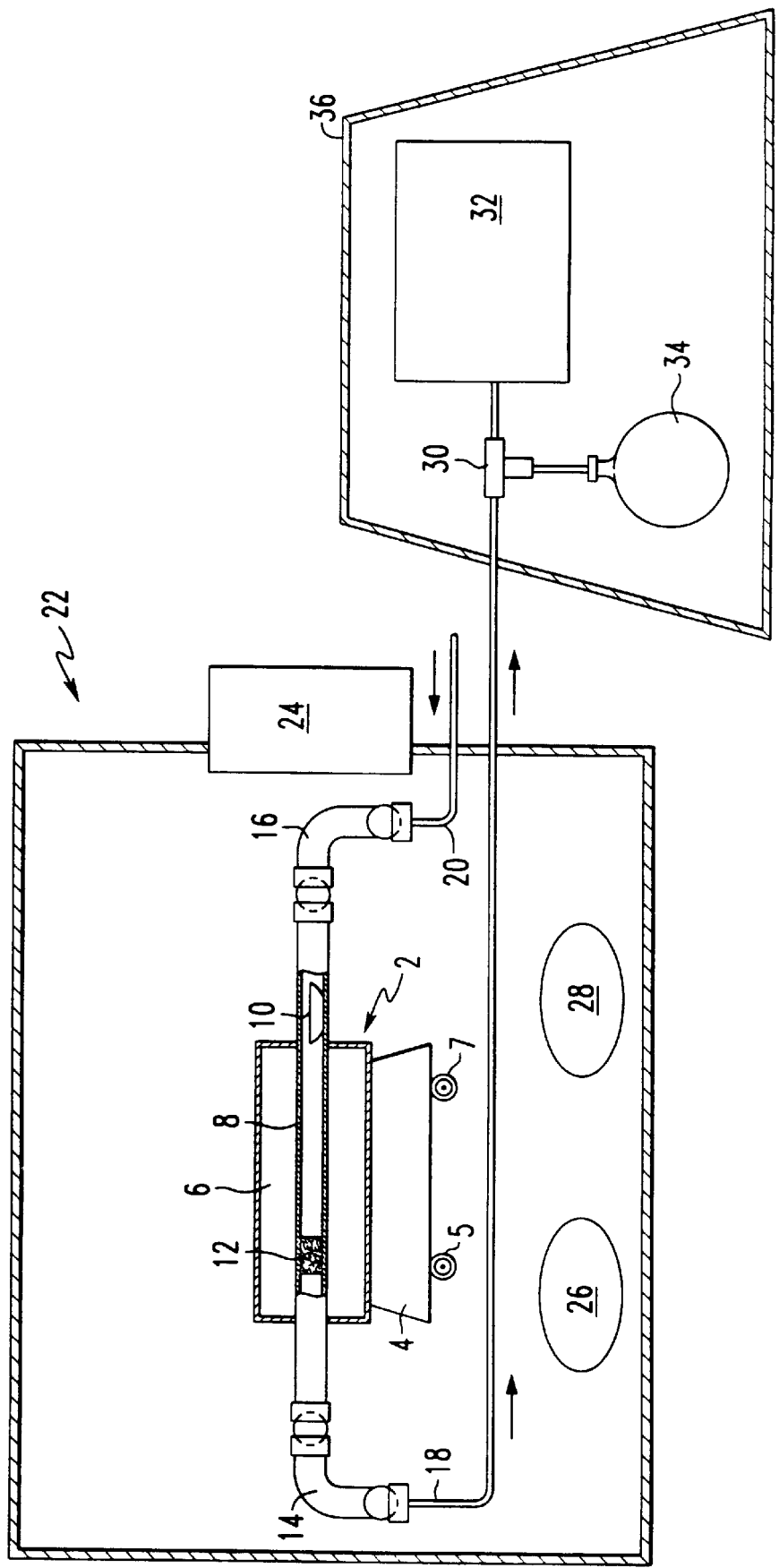
FIG. 1 is a schematic diagram of one embodiment of the apparatus according to the present invention.

The present invention relates to a method for determining hydrogen content in a compound generally comprising the steps of heating a sample of the compound at conditions sufficient to effect pyrolytic conversion of any hydrogen containing compounds in said sample to hydrogen gas, and measuring the hydrogen gas generated by the conversion. A preferred embodiment comprises the steps of inerting and purging a furnace with a noble gas whose properties are different from hydrogen at low levels; placing an uncontaminated, anhydrous sample of the compound in the furnace; heating the sample in the presence of the noble gas to effect pyrolytic conversion of any hydrogen in the sample; and determining the hydrogen content of the sample by gas chromatography using the noble gas as the carrier. Heating the sample at temperatures at or above about 1100° C. for a period of between about 3 and 7 hours is generally sufficient to cause any hydrogen in the sample to evolve.

The present invention can be used to test any waste or other sample that contains, or is believed to contain, hydrogen or a hydrogen bearing compound such as organic compounds, other hydrocarbons, waters of hydration, and/or most inorganic hydrogen. The methods of the present invention are particularly applicable to testing steam reformed nuclear residues, such as those resulting from the treatment of power plant fuel-pool radwaste. Other waste compounds include, for example, hospital, pharmaceutical or other biomedical wastes, nuclear power plant EDTA waste, and slurry wastes containing various solvents and actinides.

Steam reforming of a waste destroys hydrocarbons, removes waters of hydration, and decomposes most inorganics containing hydrogen in the waste being treated. Steam reforming detoxification provides a method for noncombustively decomposing organic compounds, comprising passing a gaseous mixture of the organic compounds and water into a reactor which includes a reaction zone having a temperature range between about 200° C. and 1820° C. to noncombustively decompose the organic compounds in the gaseous mixture, maintaining the ratio of water to organic compounds present in said gaseous mixture in said reaction zone such that the amount of water is greater than the stoichiometric amount necessary to combine with 100% of the organic compounds present in the gaseous mixture, and maintaining a residence time and mixing of said gaseous mixture and said water in said reaction zone to react substantially all of said organic compounds with said water to produce carbon monoxide and hydrogen as reaction product. By employing the steam in excess of stoichiometry, a disassociation reaction of the organic compound with the water is effected; carbon dioxide, carbon monoxide and hydrogen are formed as by-products. A steam reforming detoxification method and apparatus are further described in U.S. Pat. No. 4,874,587, which is hereby incorporated by reference in its entirety. Optimum steam reforming conditions are typically 900°–1100° C. with steam over 31% molar excess and residence times of about 1.5 seconds.

Prior to employing the methods of the present invention, it is important that the sample be kept as dry as possible; hydration of the sample, even by the air in the room, can lead to inflated and therefore unacceptable hydrogen readings. Preferably, the sample undergoes a drying step prior to testing. For example, the sample can be nitrogen dried by flowing $N_2$ instead of steam through the steam reformer. Any other suitable drying means can also be used. Following drying of the sample, it is important to store the sample in such a way as to ensure that the sample will not become contaminated with moisture from the air, as this moisture could form radiolytic hydrogen during testing. Preferably, the sample is taken of the treated waste in dry, room air-free conditions, stored in a desiccator, and transported to the analytical apparatus. The dessicator can then be placed in the inerted glove box, and the sample removed when testing is to begin.

The methods of hydrogen determination according to the present invention are preferably carried out in a high temperature quartz tube furnace enclosed in an inerted, dry glove box, such as the apparatus shown in FIG. 1. Any other type of suitable furnace can also be used. The tube furnace 2 is comprised of a movable bottom portion 4 and an electrically heated top portion 6. Preferably, the furnace portion 4 surrounding the tube is equipped with wheels 5 and 7, and can be moved within the glove box. The furnace was used to quickly heat the sample once the sample was inserted and the gas chromatograph baseline determined. Extending through the length of top portion 6 is a quartz tube 8, approximately 1–2 inches in diameter, into which can be placed a sample boat 10. Any suitable tube can be used; quartz is preferred as it is pure and contains no hydrogen. In a preferred embodiment, a carbon plug 12 is placed inside quartz tube 8. The carbon plug 12 functions to convert any of the water that might be evolved into hydrogen gas by means of a steam-carbon reaction, forming carbon monoxide and small amounts of carbon dioxide. A vapor-phase granular activated carbon, commercially available from Calgon Carbon, Pittsburgh, Pa., is suitable for this use; any other type of carbon that will convert water can also be used. The quartz tube 8 is attached at either end to joints 14 and 16. Joints 14 and 16 are ground glass ball and socket joints; no organic grease is used. Joints 14 and 16 connect the quartz tube 8 to a suitable metal tubing, such as ⅛" stainless steel tubing 18 and 20. Any other suitable tubing could also be used so long as gas can be circulated from a gas source, such as a gas tank, through the tube furnace. The arrows represent the flow of gas through the quartz tube 8 and tubing 18 and 20. Gas flows from a gas tank or other source (not shown) through tubing 20, the quartz tube 8 and tubing 18 out of the glove box. As is illustrated in the embodiment represented by FIG. 1, tubing 18 is attached to joint 30. Gas travels through joint 30 either to gas chromatograph 32 contained in inert tent 36 or a gas collection bag 34. The gas chromatograph, which is preferably a micro gas chromatograph with minimum sensitivity of at least 100 ppm hydrogen, continuously samples the gas over the whole heating cycle and can also be contained in glove box 22. The gas collecting bag 34 is preferably made from tedlar® or any other suitable material, and is used to collect the total gas sample and separately supply the gas chromatograph following the test run of the sample as a check on the integration of the continuously sampled gas. The entire furnace is contained within an inert glove box 22, having a pass-through port 24 and one or more glove ports, represented at 26 and 28.

The glove box 22 and tube furnace 2 should be inerted and purged prior to use in the present methods. This is done by purging the glove box and tube furnace prior to sample insertion. At steady state, the glove box water content is below the level of detection. The tube furnace is preferably heated overnight so that it, and the carbon bed, achieve low hydrogen and water background levels before the sample is inserted. This helps to ensure against contamination of the sample through atmospheric or instrumentation background hydrogen and moisture. Because the gas with which the box and furnace are inerted and purged will also be the gas used as the carrier in the gas chromatograph, a gas whose properties are sufficiently different than hydrogen at low levels should be used. Preferred for this use are the noble gases, most preferably argon. Typically, argon will provide a higher sensitivity during chromatography than the other noble gases because of the thermoconductive difference between it and hydrogen. The sensitivity can also be adjusted by increasing or decreasing the amount of gas used, with lower amounts resulting in a higher sensitivity because of less dilution of the hydrogen to be detected.

Preferably, a dessicator containing the sample is placed in the inerted glove box through pass through port 24. The dried sample is removed from its dessicator in the glove box and inserted in the tube furnace. Preferably, joint 16 is removed and the dried sample, placed in a quartz boat 10, is slid into the quartz tube 8. The joint 16 is then reattached and the gas flow commenced. Preferably, the gas flow is maintained between about 10 and 15 cc/min. A background base is established after about 5 to 10 minutes, and the furnace is slid over the boat. Gas flow should be continued throughout the remainder of the procedure, so that the gas flows over the sample.

Heating is preferably done quickly to avoid coking, starting at about 100° C. and extending up to a temperature of about 1100° C., or the maximum of the furnace, whichever is higher. The temperature ramp reveals the progress of the evolution of moisture, then waters of hydration in the sample, and then hydrogen cracking. The hydrogen determination is made by the gas chromatograph about every 4 minutes throughout the run, with a gas flow of preferably about 10 ml/min. Measurements can be taken at any interval desired by the user.

Waters of hydration cannot be removed by a simple aqueous oxidation process, such as those involving hydrogen peroxide or other non-thermal methods. The waters of hydration can only be removed by a much more severe, high temperature thermal step that actually pulls the waters of hydration from their parent compounds. Removal of such waters is effected at temperatures up to about 500° C. Thus, exposure of the sample above this level to about 1100° C. essentially simulates conditions under which radiolytic decomposition of hydrogen containing compounds will occur. Any water evolution is expected to be the result of adsorbed moisture from the air during sample transfer plus any water that is left from the steam-reforming followed by dry gas purging.

The time for heating will vary depending on the sample being tested, the temperature regime being employed and the needs of the user. In general, heating should be performed for a sufficient time to effect pyrolytic conversion of any hydrogen-containing compounds in the sample to hydrogen gas; typically heating should be effected for at least about 5 hours. If a baseline level of hydrogen for the unit is determined before inserting the sample and sliding the furnace over the sample, heating can be stopped when the hydrogen levels being recorded are near the initial baseline level. This would indicate that all or nearly all of the hydrogen has been evolved.

Because of the low levels of hydrogen in the samples being tested, and the need for a method that is highly sensitive for these hydrogen levels, a micro gas chromatograph should be used with minimum sensitivity of 100 ppm hydrogen. Suitable micro gas chromatographs are commercially available from MTI Analytical Instruments, Fremont, Calif. The small size and portable nature of these devices makes them well suited for placing in the inerted box and use in the field. Also, because of the concerns of atmospheric humidity or other moisture contaminating the sample, the gas chromatograph is preferably contained within the inerted glove box. The micro gas chromatograph, being a rapid cycle device, is also well suited for nearly continuous hydrogen measurements.

EXAMPLES

The following examples are intended to illustrate the invention, and should not be construed as limiting the invention in any way.

Examples 1–3

A surrogate sample was prepared that was representative of nuclear waste to be processed. Three different samples of this surrogate waste were steam reformed at different conditions, that is at different temperatures for different amounts of time. Sample 1 was steam reformed at the lowest severity with temperatures reaching about 900° F. and a processing residence time of about 5 hours. Sample 2 was treated at medium severity as compared with Samples 1 and 3 lasting for about 15 hours at about 960° F. Sample 3 was treated with the highest severity, lasting for about 30 hours with ramping from 940° F. to about 1030° F. Samples were taken of the finished residue product in completely inerted equipment with tented DFE doorway by operators in self-contained suits. These residue samples were dried with nitrogen gas for a period of about 3 hours and stored in a desiccator while still inert prior to testing. These sealed dessicators were taken from the inert tent and taken to the gas chromatograph lab. During surrogate waste sample steam reforming, equipment was maintained at low (<3%) levels of oxygen, about 2000 ppm carbon dioxide, <200 ppm carbon monoxide and about 2000 ppm hydrogen production during treatment of these samples.

In addition to testing the three steam-reformed residue product samples, a sample blank, a trip blank sample using anhydrous $Na_2SO_4$, and a phenanthrene sample were treated. The "trip" blank involved treating and handling the $Na_2SO_4$ in the same manner as the steam-reformed surrogate waste samples. Anhydrous $Na_2SO_4$ is very sensitive to water contamination, and its analysis indicates how much, if any, water contamination occurred during handling and treatment of the samples. Each of the samples was tested in the quartz tube furnace shown in FIG. 1. The quartz tube furnace and the gas flow tubing were placed inside of a 1 meter long inerted glove box. At one end of the quartz tube, within the heated zone, a 1 inch long bed of carbon chips was packed between 2 wads of quartz wool. This carbon bed functioned to convert any of the water evolved during heating of the samples into hydrogen gas by means of the steam-carbon reaction, forming carbon monoxide and a little carbon dioxide; this is beneficial because there is a greater sensitivity to hydrogen gas than hydrogen in a water molecule. The extent of the water reaction was monitored by measuring the carbon monoxide level. This separate determination of water produced from the sample allowed discrimination from any water that diffused into the outlet tubing, the TEDLAR® sample bags. The TEDLAR® bags allowed for collection and transfer of gas from the bag to the gas chromatograph by pulling gas out of the bag into the gas chromatograph with the gas chromatograph sample pump. This was done after testing of the sample, to ensure the accuracy of continuous readings done throughout testing.

First, a background curve was obtained for hydrogen gas flowing through the quartz tube to observe its decay rate and data scatter. In about 1 hour, the hydrogen dropped from about 221 ppm to about 160 ppm. The quartz tube purge rate of argon was between about 18 and 19 ml/min. The glove box purge rate of argon was 8 liters/min. The decay rate of hydrogen was determined as follows. A new, clean quartz boat was removed from a plastic container stored with desiccant. The inlet end of the quartz tube 35/25 joint was removed, as was the small quartz wool plug, and the empty boat was inserted to about 1 inch just outside of the heated zone of the furnace. With the boat in the tube, the joint was replaced, the quartz wool plug was returned and the tube was sealed. After the baseline curve was determined, the furnace was slid to the right to fully surround the quartz boat, at which time the quartz boat began to heat quickly and gas began to collect in the TEDLAR® bag.

A moving furnace approach was used because the handling process of inserting an empty quartz boat into the quartz tube included the unavoidable introduction of vibration into the carbon bed. When the carbon bed was disturbed, fresh carbon surfaces were exposed which caused new evolution of hydrogen gas, carbon monoxide and water. The movable furnace also allowed more room for the joint to be removed to allow for insertion of the sample into the tube. After about 1.28 hours, the furnace was slid to the left and no longer surrounded the empty boat. The boat was allowed to cool for about 30 minutes, after which time it was removed. Following removal of the boat, the joint was replaced quickly on the tube to avoid contamination from the glove box atmosphere.

Figure 2:
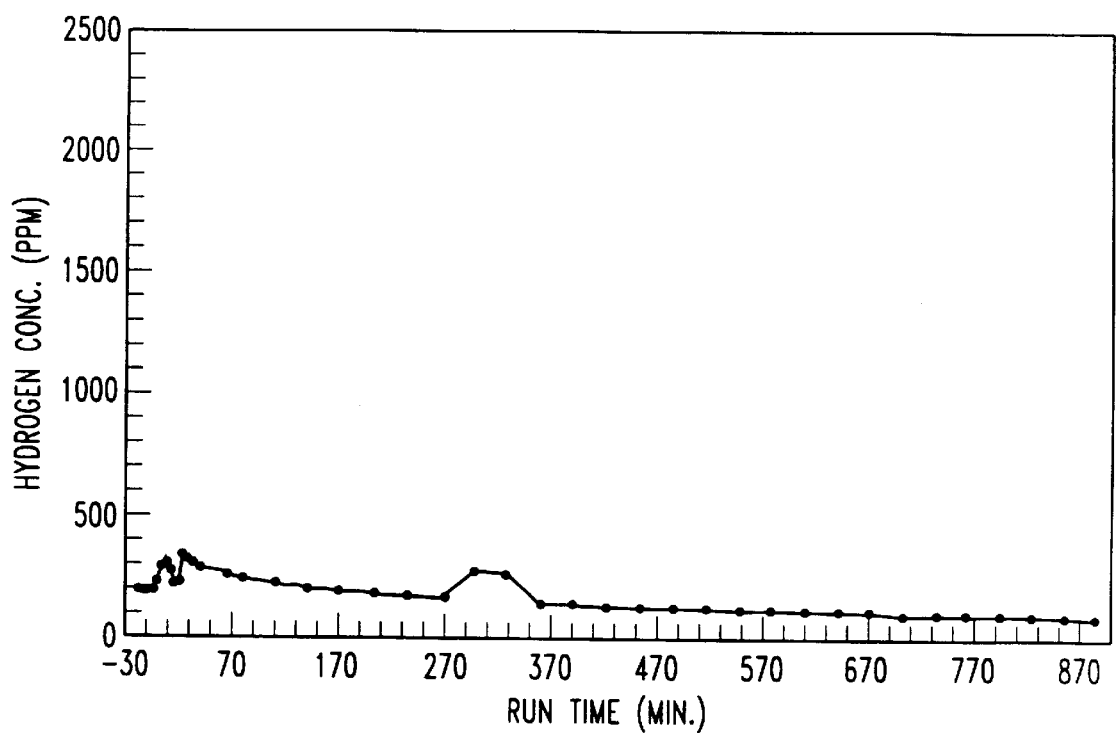
FIG. 2 is the background curve generated for hydrogen from the empty boat and quartz tube.

The background curve for hydrogen gas evolution from the empty boat and quartz tube provided an estimate of the baseline curve that must be subtracted from the hydrogen production curve generated by each of the various samples in their respective boats. This background curve is shown in FIG. 2. The hydrogen calibration curve was determined using NIST traceable standards at either 100 or 500 ppm and was run prior to and following every gas chromatograph run to set the scale factor for the gas chromatograph output.

Figure 3:
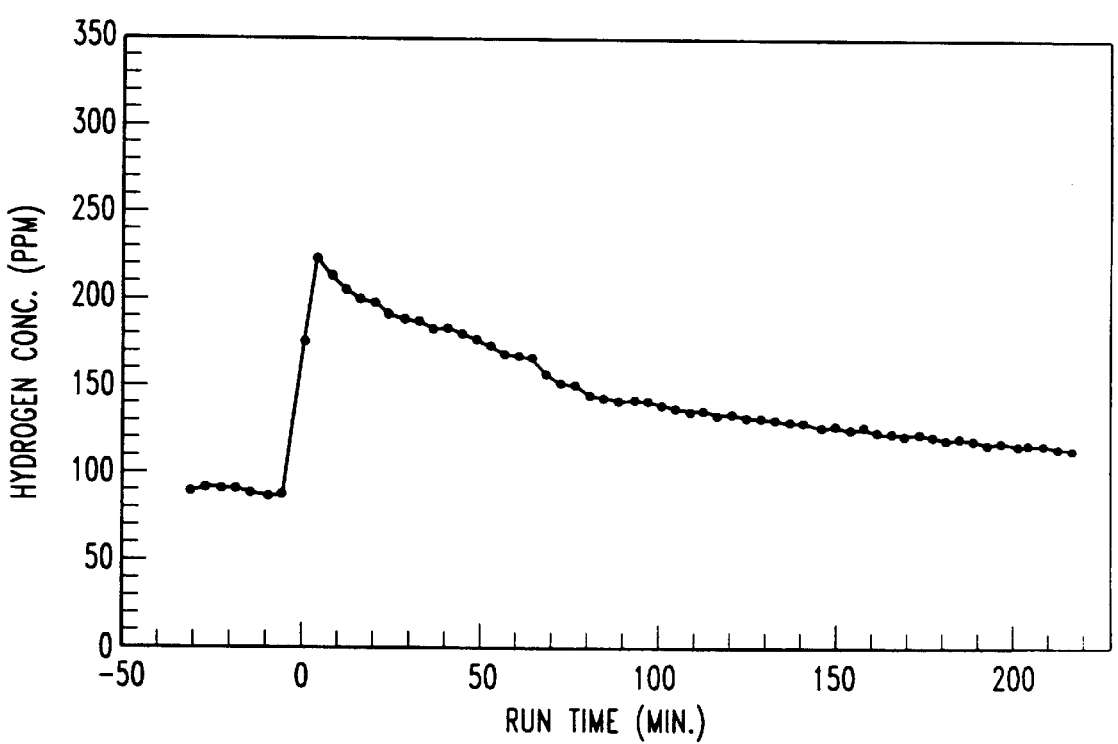
FIG. 3 graphically illustrates the amount of hydrogen generated by the $Na_2SO_4$ sample.

A trip blank test was then performed using the analytical reagent anhydrous $Na_2SO_4$. The $Na_2SO_4$ was treated in the same manner that the samples were throughout all of the steam-reforming handling steps. This was done to reflect the actual amount of moisture that the samples would pick up as the result of the many handling steps involved. The $Na_2SO_4$ was loaded into the quartz boat within the inerted glove box, which had a hydrogen gas level below about 12 ppm. The quartz boat containing the $Na_2SO_4$ was then loaded into the quartz tube as described above for the sample blank. The furnace was immediately slid to the right to fully surround the boat, at which point the $Na_2SO_4$ and quartz boat began heating quickly and gas collection in the TEDLAR® bag began. As the $Na_2SO_4$ heated, the water, hydrogen gas and other gas evolutions increased after about 10 minutes. The entire run was about 3.33 hours long, and gas sampling and gas chromatograph operation cycle was once every 4 minutes. After this time, the furnace was moved back and the boat was allowed to cool briefly before being removed. The sealed quartz tube was then allowed to bake out overnight at a temperature of approximately 1100° C. FIG. 3 graphically illustrates the amount of hydrogen generated by the trip blank of $Na_2SO_4$. The amount of water picked up from the trip blank was equivalent to about 20 ppm hydrogen averaged over a gas evolution time of about 50 minutes, this was equivalent to only about 2.8 microgram moles of hydrogen, which was considered to be a negligible amount. These corrections are subtracted from the amount of hydrogen determined by the gas chromatograph and normalized to get the amount of hydrogen in the surrogate waste sample mass treated by steam-reforming.

Figure 4:
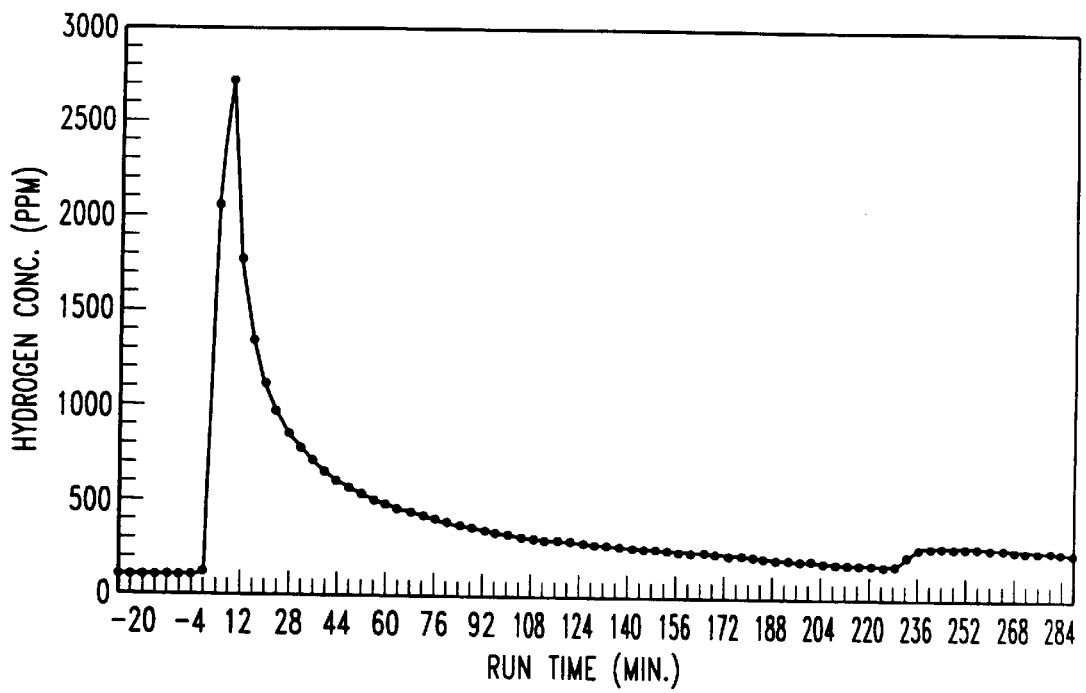
FIG. 4 graphically illustrates the amount of hydrogen generated by Sample 1.

About 14.5 g of Sample 1 were then placed into the clean quartz boat. The tube background level was 91 ppm hydrogen. The run began at 12:57 hours and evolved hydrogen gas for about 5½ hours; by 18:25 hours the hydrogen gas level had decreased and was at the extrapolated baseline level of 228 ppm and did not change after several 4 minute sample intervals. The run was then stopped. Approximately 6 liters of gas was collected in the TEDLAR® bag. The gas chromatograph integrated hydrogen level plus baseline was 418.7 ppm and the TEDLAR® gas bag measured 389 ppm hydrogen. Subtracting the baseline at an average value of 91 ppm as the lowest and most conservatively low value, the result was about 298 ppm or about 0.0376 gmoles of hydrogen. FIG. 4 shows the hydrogen gas data as a function of time. The true baseline was probably somewhere between 91 and 228 ppm, so if anything greater than 91 was subtracted a slightly lower value of gmoles of hydrogen in the treated residue would be calculated.

Figure 5:
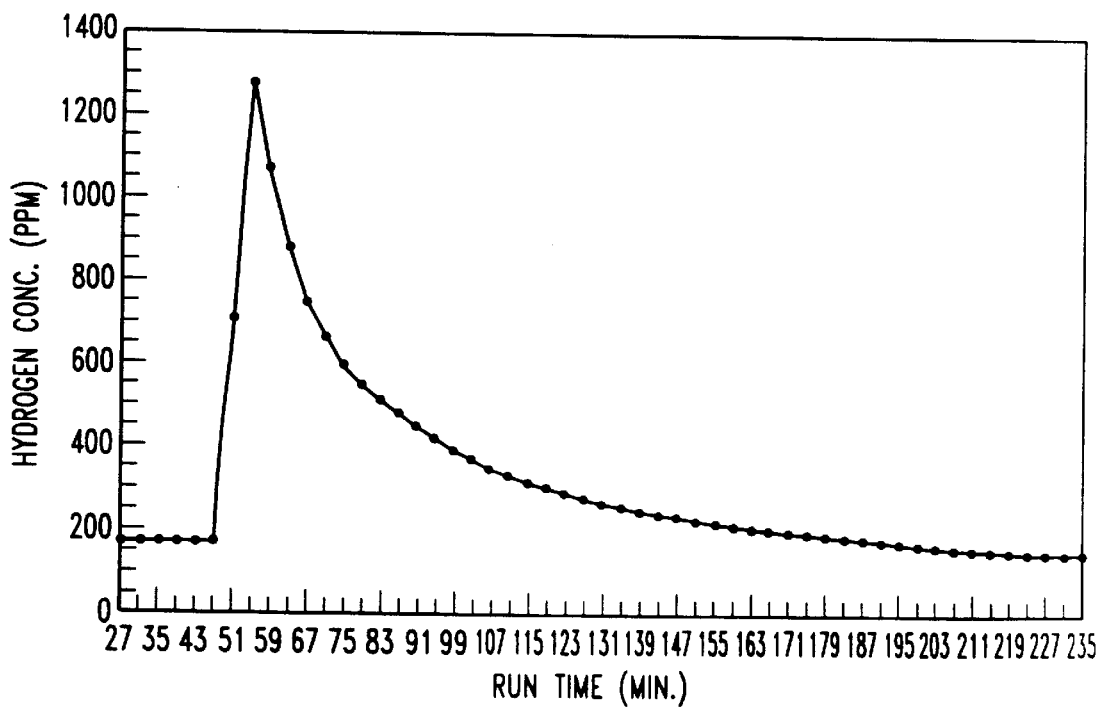
FIG. 5 graphically illustrates the amount of hydrogen generated by Sample 2.

Sample 2 was then tested in the same manner. FIG. 5 shows the hydrogen gas data as a function of time from the start of the run at about 11:45 hours. By 14:58 hours, the hydrogen level was below the extrapolated baseline of 150 ppm and the run was stopped. About 3.55 liters of gas were collected in the bag. The integrated level plus baseline was 341.6 ppm hydrogen and the tedlar® gas bag measured about 334 ppm hydrogen. Subtracting the baseline at an average value of 160 ppm, the result ranges from 174 to 181.6 ppm, or about 0.0260 gmoles of hydrogen.

Figure 6:
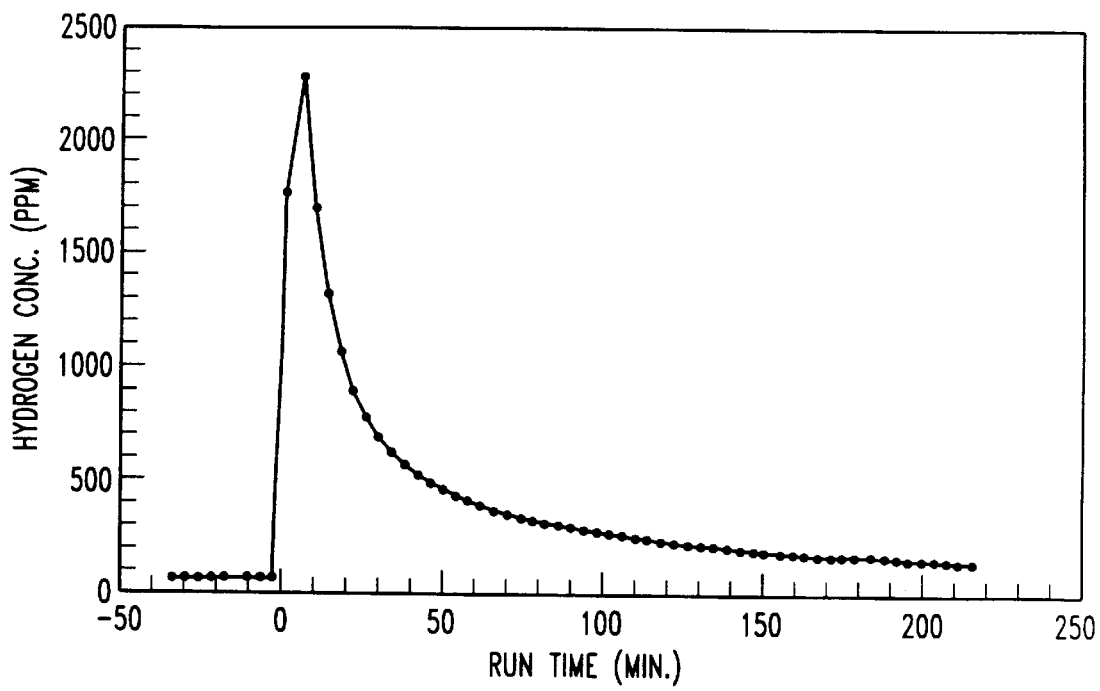
FIG. 6 graphically illustrates the amount of hydrogen generated by the duplicate run of Sample 2.

A duplicate run using Sample 2 was performed. FIG. 6 shows the hydrogen data as a function of time from the start of the run at 13:22 hours. By 16:56 hours, the hydrogen gas level was below the extrapolated baseline of 138.1 ppm and the run was stopped. Again, about 3.55 liters of gas was collected in the bag. The gas chromatograph integrated level plus baseline was 414.8 ppm hydrogen and the gas bag measured 388 ppm hydrogen. Subtracting the lowest possible conservative baseline at an average value of 67 ppm, the result was about 321 ppm or about 0.0267 gmoles of hydrogen. This was approximately the same as the first run of Sample 2.

Figure 7:
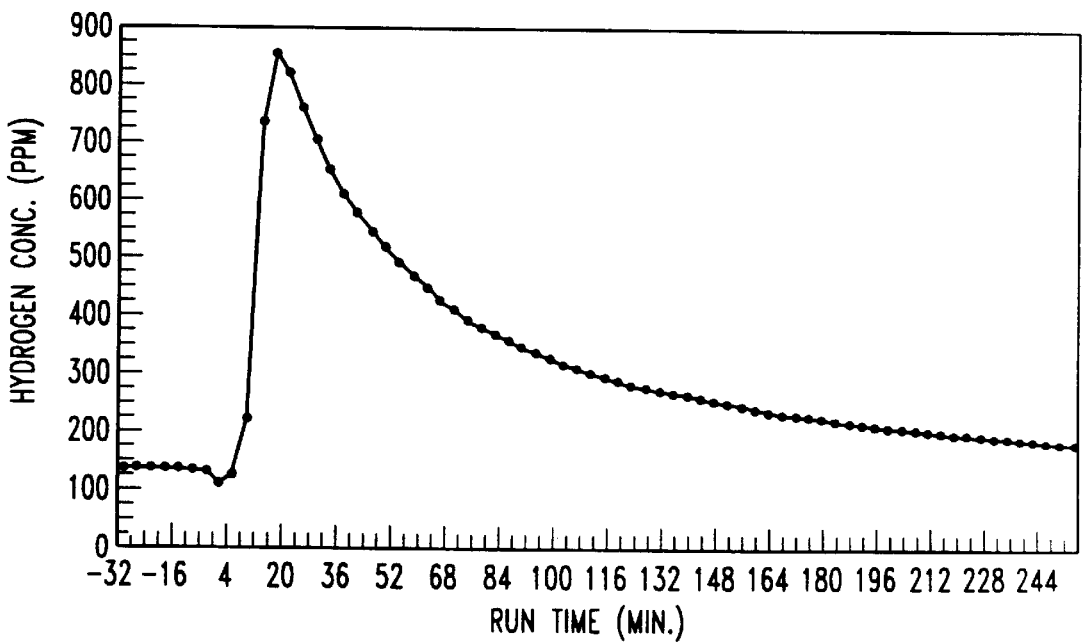
FIG. 7 graphically illustrates the amount of hydrogen generated by Sample 3.

Sample 3 was then tested in the same manner as the previous samples. FIG. 7 shows the hydrogen data as a function of time from the start of the run at 10:42 hours. By 16:03 hours, the hydrogen gas level was at 161.5 ppm and was only changing about 0.2 ppm/minute. This was near to the extrapolated baseline of 131.6 ppm and the run was stopped. About 6 liters of gas were collected in the bag; the gas chromatograph integrated level plus baseline was 297.8 ppm hydrogen and the tedlar® gas bag measured about 294.1 ppm hydrogen. Subtracting the lowest possible conservative baseline at an average value of 131 ppm, the result is 163.1 ppm hydrogen, or about 0.0243 gmoles of hydrogen.

Figure 8:
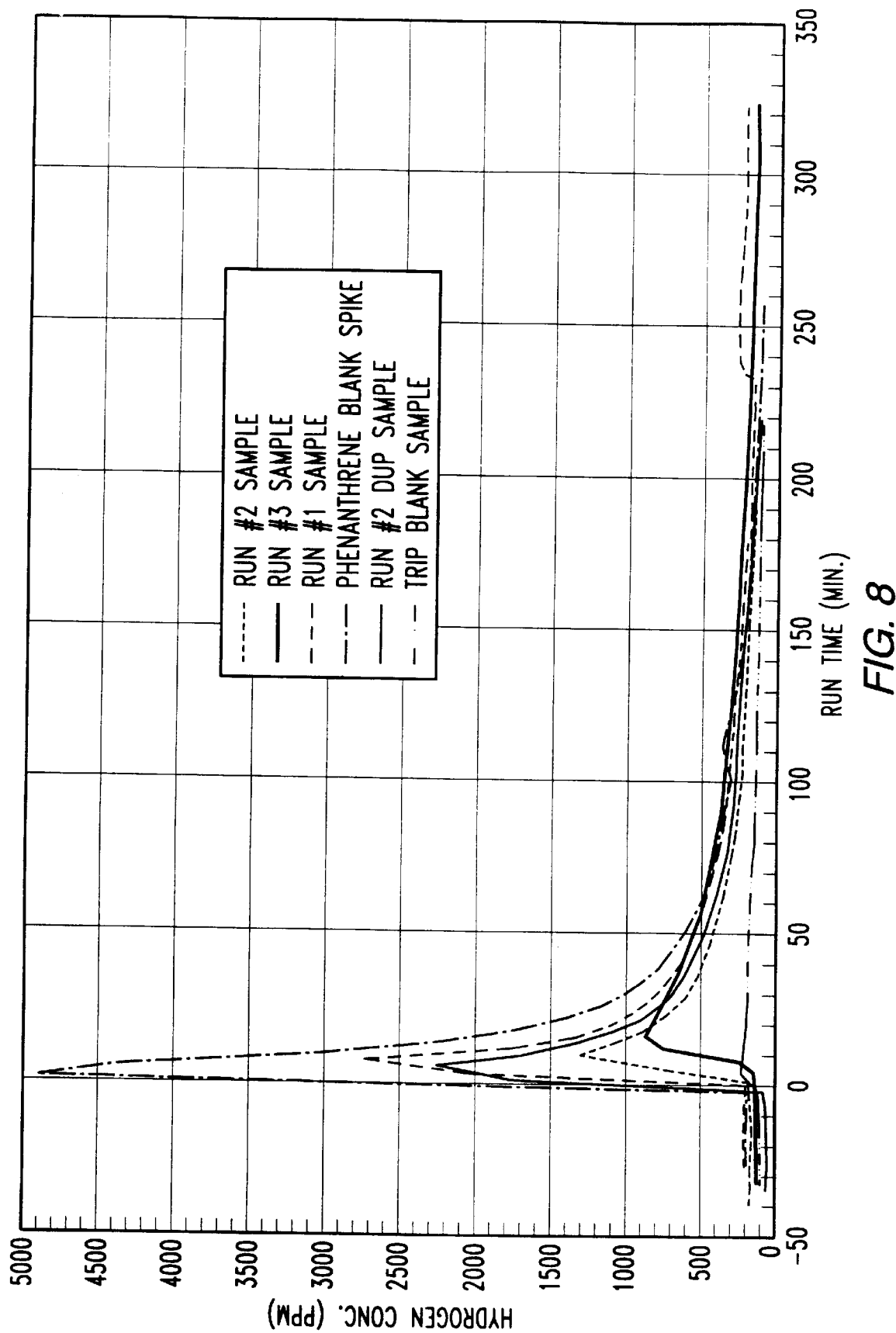
FIG. 8 graphically illustrates the amount of hydrogen generated by Samples 1, 2, 3, $Na_2SO_4$ and phenanthrene.

Finally, a sample of phenanthrene was run. Phenanthrene is an analytical reagent with accurately known hydrogen content equal to the NRC critical quantity for nuclear plant waste. This sample, therefore, represented the maximum quantity of hydrocarbon allowed by the NRC for disposal casks. FIG. 8 compares the hydrogen content of the phenanthrene sample with those of the steam reformed samples and the $Na_2SO_4$. The phenanthrene sample had significantly higher amounts of hydrogen than any of the other samples tested. Accordingly, all of the steam reformed samples had sufficiently low hydrogen levels to meet NRC requirements.

The residue hydrogen content in each of the steam reformed residues and trip blank samples was calculated based on the mass of the residue taken out of the can feeder evaporator (CFE), the measured hydrogen level collected in the TEDLAR® gas bag, the volume of argon-hydrogen mixture in the gas bag, the density of the gas in the sample bag at laboratory temperature and pressure, the mass of the residue sample placed into the quartz furnace boat and the molecular weight of atomic hydrogen, $H_1$, as follows:

$$\genfrac{}{}{0pt}{}{\text{gmoles } H_1}{\text{in residue}} = 2 \cdot \frac{(\text{gm residue}) \cdot (H_2 \text{ in bag, ppm} - lH_2/l\text{bag}) \cdot (\text{Bag Vol. } l_{bag}) \cdot (\rho \cdot \text{gm}H_2/lH_2)}{1 \times 10^6 \cdot (2.01594 \text{ gm}H_2/\text{gmole}H_2) \cdot (\text{gm boat sample})}$$

where:

l=liters of gas, and $\rho$=gas density calculated by: $\rho = P \cdot Mw/R \cdot T$ (typically around 0.083 $gmH_2/lH_2$)

where:

P=1 atmosphere (with small correction for 1100 ft. altitude

Mw=molecular weight of $H_2$=2.01594

R=Universal Gas Constant=0.08205 l·atmos/gmole·°K.

T=Absolute Temperature °K. (approximately 294.82°K.)

A summary of the calculated hydrogen levels is presented in Table I below:

TABLE 1

Residue Hydrogen, $H_1$, Content

| SAMPLE | Sample Mass (gms) | Residue stuck in CFE (% estimate) | Residue in CFE (gms) | $H_1$ Content (gmoles) |
|---|---|---|---|---|
| 1 | 3680.85 | 0.10 | 3684.53 | 0.0376 |
| 2 | 3703.14 | 1.00 | 3740.17 | 0.0260 |
| 2 (dupl) | 3703.14 | 1.00 | 3740.17 | 0.0267 |
| 3 | 3565.19 | 5.96 | 3777.68 | 0.0243 |
| trip blank | 6.821 | — | — | 0.0099* |

*This content was calculated from the measured content of $2.8 \times 10^{-6}$ gmoles $H_2$ normalized to a typical residue sample size of 3600 gms.

The significance of the residue hydrogen determinations in Table 1 is that if the real waste is processed under steam-reforming treatment in the manner of Sample #2, about 5 times the mass or residue (about 18 kg) could safely be placed in the NRC cask.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for determining hydrogen content in a compound comprising:

heating an uncontaminated, anhydrous sample of said compound at temperature at or above about 1100° C. for a period of between 3 and 7 hours to effect pyrolytic conversion of any hydrogen containing compounds in said sample to hydrogen gas; and measuring the hydrogen gas generated by said conversion.

2. The method of claim 1, wherein said heating step is carried out in a furnace in the presence of a noble gas.

3. The method of claim 2, wherein said hydrogen content of said sample is measured by gas chromatography using said noble gas as the carrier.

4. The method of claim 3, wherein said hydrogen measuring step is repeated about every 4 minutes.

5. The method of claim 3, wherein said gas chromatography is accomplished with a micro gas chromatograph having a sensitivity of at least 100 ppm.

6. The method of claim 3, wherein said furnace is a tube furnace and wherein said noble gas is circulated through said tube furnace to said gas chromatograph so as to transport said generated hydrogen gas to said gas chromatograph.

7. The method of claim 6, further including the step of placing a carbon plug in said tube furnace through which said hydrogen gas passes when being circulated to the gas chromatograph.

8. The method of claim 2, wherein said noble gas is argon.

9. The method of claim 2, wherein said furnace is contained within an inerted and purged glove box.

10. The method of claim 9, wherein said sample is contained in a dessicator, said dessicator is placed into said glove box and transferred from said dessicator into said furnace.

11. The method of claim 2, further including the step of drying said sample prior to placing it in said furnace.

12. The method of claim 11, wherein said compound is a steam reformed nuclear waste residue and said drying step is accomplished by drying said sample with nitrogen gas circulated through the steam reforming process stream.

13. The method of claim 1, wherein said compound is a steam reformed nuclear waste residue.

14. The method of claim 13, wherein said nuclear waste residue has been steam reformed at a temperature of between about 500° and 900° C. for between about 5 and 15 hours.

15. The method of claim 13, wherein the waste is organic compounds.

16. An apparatus for determining hydrogen content in a compound comprising:

a furnace for heating a sample of said compound at temperatures at or above about 1100° C. for a period of between 3 and 7 hours to effect pyrolytic conversion of any hydrogen containing compounds in said sample to hydrogen gas;

a gas chromatograph attached to said furnace; and a means for circulating gas from a gas source through said furnace to said gas chromatograph.

17. The apparatus of claim 16, wherein said furnace is a tube furnace.

18. The apparatus of claim 17, wherein said tube furnace further comprises a heated top portion through which said tube extends and a movable bottom portion movable along the length of said tube.

19. The apparatus of claim 16, wherein said gas circulating means includes a pressurized gas source and a gas chromatograph pump wherein said gas is circulated from said gas source to said gas chromatograph.

20. The apparatus of claim 19, wherein said gas chromatograph is a micro gas chromatograph.

21. The apparatus of claim 20, wherein the furnace is a quartz tube furnace.

* * * * *